(12) United States Patent
Fujioka et al.

(10) Patent No.: US 10,202,576 B2
(45) Date of Patent: Feb. 12, 2019

(54) APPARATUS FOR CULTURING CELLS

(71) Applicant: Panasonic Intellectual Property Management Co., Ltd., Osaka (JP)

(72) Inventors: Soichiro Fujioka, Osaka (JP); Takeshi Ando, Kyoto (JP); Toshinori Hirose, Osaka (JP); Norihiro Shibata, Osaka (JP); Osamu Mizuno, Nara (JP); Toshiaki Yamauchi, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 342 days.

(21) Appl. No.: 14/891,997

(22) PCT Filed: Dec. 22, 2014

(86) PCT No.: PCT/JP2014/006369
§ 371 (c)(1),
(2) Date: Nov. 18, 2015

(87) PCT Pub. No.: WO2015/098081
PCT Pub. Date: Jul. 2, 2015

(65) Prior Publication Data
US 2016/0090570 A1    Mar. 31, 2016

(30) Foreign Application Priority Data

Dec. 27, 2013  (JP) ................. 2013-271273

(51) Int. Cl.
*C12M 1/00*      (2006.01)
*C12M 1/26*      (2006.01)
(Continued)

(52) U.S. Cl.
CPC ............ *C12M 41/48* (2013.01); *C12M 23/48* (2013.01); *C12M 23/50* (2013.01); *C12M 29/00* (2013.01); *C12M 33/04* (2013.01)

(58) Field of Classification Search
CPC ...... C12M 29/00; C12M 41/04; C12M 41/08; C12M 23/48; C12M 23/50; C12M 33/04
See application file for complete search history.

(56) References Cited

U.S. PATENT DOCUMENTS 3,844,896 A     10/1974   Sharpe
2006/0275888 A1  12/2006   Hibino et al.
(Continued)

FOREIGN PATENT DOCUMENTS

JP    2004-305148    11/2004
JP    2007-024576    2/2007
(Continued)

OTHER PUBLICATIONS

International Search Report of PCT application No. PCT/JP2014/006369 dated Apr. 7, 2015.
(Continued)

*Primary Examiner* — Gautam Prakash
(74) *Attorney, Agent, or Firm* — Panasonic IP Management

(57) ABSTRACT

An apparatus for culturing cells of the present invention is an apparatus for culturing cells using a culture medium in a culture vessel. The apparatus includes: pump connected to pipet held by first holder; first shifter configured to shift first holder; second holder configured to hold culture vessel; second shifter configured to grip and shift culture vessel; and controller. Controller is programmed to, when pipet draws a liquid in culture vessel or discharges a liquid into culture vessel, control second shifter to translationally shift lid of culture vessel in a horizontal direction.

8 Claims, 8 Drawing Sheets

(51) Int. Cl.
C12M 1/36 (2006.01)
C12M 3/00 (2006.01)

(56) References Cited

U.S. PATENT DOCUMENTS

2007/0015272 A1 1/2007 Ogura et al.
2013/0017127 A1 1/2013 Tokumaru
2014/0030168 A1 1/2014 Tokumaru et al.

FOREIGN PATENT DOCUMENTS

JP 2012-152124 8/2012
JP 2013-017461 1/2013
WO 2012/132148 10/2012

OTHER PUBLICATIONS

The Extended European Search Report dated Jun. 1, 2016 for the related European Patent Application No. 14873295.1.

APPARATUS FOR CULTURING CELLS

This application is a U.S. national stage application of the PCT International Application No. PCT/JP2014/006369 filed on Dec. 22, 2014, which claims the benefit of foreign priority of Japanese patent application 2013-271273 filed on Dec. 27, 2013, the contents all of which are incorporated herein by reference.

TECHNICAL FIELD

The present invention relates to cell culture.

BACKGROUND ART

Generally, cells are cultured using a culture medium. The culture medium is a culture solution containing a large amount of nutrients. As the culture medium is used for a long period, the pH of the culture medium drops under the influence of lactic acid or the like produced by cell growth. When the pH of the culture medium drops, the pH may deviate from the pH range suitable for cell culture, causing cell culture inactive. Accordingly, with a conventional apparatus for culturing cells, the culture medium is replaced at certain time intervals in accordance with the type of detected cells (for example, see PTL 1).

FIG. 8 shows apparatus for culturing cells 101 disclosed in PTL 1. In connection with apparatus for culturing cells 101, in accordance with the type of cells detected by detection means 104, replacement of a culture medium by replacing means 102 or addition of a reagent by addition means 103 is performed to culture means 105. Replacement of culture medium is generally performed manually using a pipet.

CITATION LIST

Patent Literature

PTL 1: Unexamined Japanese Patent Publication No. 2007-024576

SUMMARY

Conventionally, replacement of a culture medium is based on a manual practice. Accordingly, when cell cultivation is actively performed and culture media in a multitude of culture vessels must be replaced, manual replacement of such culture media becomes difficult. An object of the present invention is to provide an apparatus for culturing cells and a method for culturing cells with which replacement of a culture medium can be automated.

In order to achieve the object stated above, an apparatus for culturing cells using a culture medium in a culture vessel is provided. The apparatus includes: a pump connected to a pipet held by a first holder; a first shifter configured to shift the first holder; a second holder configured to hold the culture vessel; a second shifter configured to grip and shift the culture vessel; and a controller programmed to, when the pipet draws a liquid in the culture vessel or discharges a liquid into the culture vessel, control the second shifter to translationally shift a lid of the culture vessel in a horizontal direction to open the lid.

Further, in order to achieve the object stated above, a method for culturing cells using a culture medium in a culture vessel is provided. The method includes: holding a pipet by a first holder; gripping and shifting the culture vessel by a second shifter; and then drawing a liquid in the culture vessel or discharging a liquid into the culture vessel by the pipet held by the first holder with a lid of the culture vessel translationally shifted in a horizontal direction by the second shifter.

According to the present invention, an apparatus for culturing cells and a method for culturing cells with which replacement of a culture medium can be automated can be provided.

DETAILED DESCRIPTION OF PREFERRED EMBODIMENTS

In the following, a description will be given of an exemplary embodiment of the present invention with reference to the drawings. Note that, identical reference marks are allotted to identical constituent elements, and a description thereof may be omitted. Note that, the drawings are schematically made while featuring respective constituent elements.

Exemplary Embodiment

Figure 1:
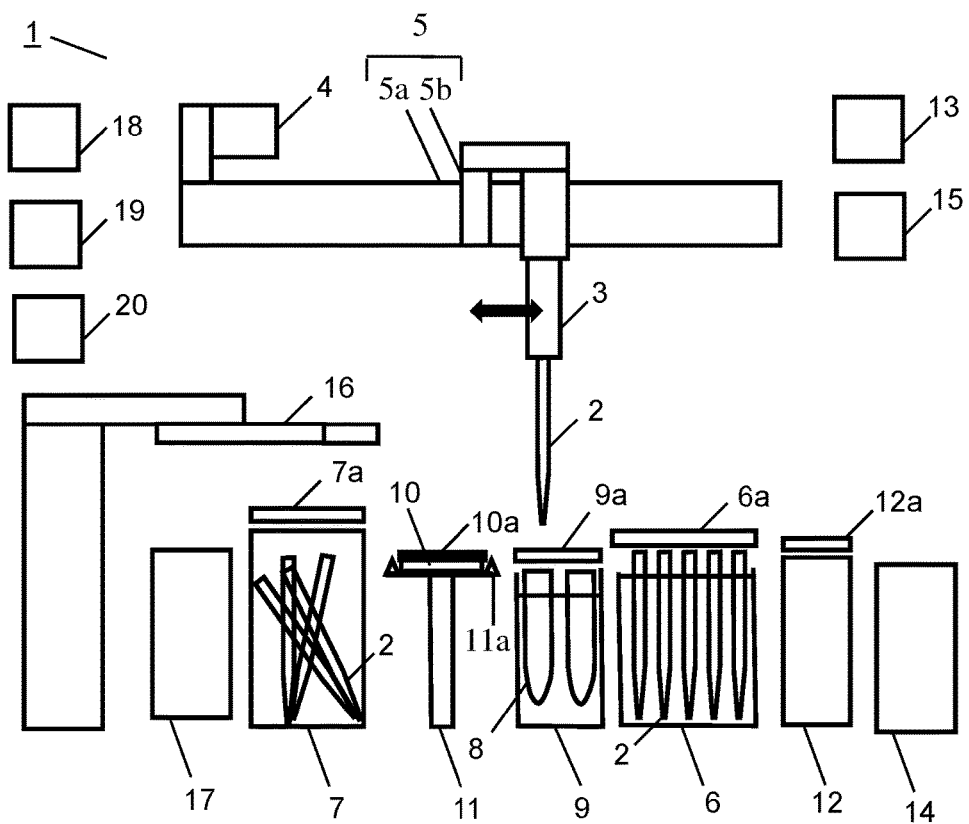
FIG. 1 is a diagram showing an overview of an apparatus for culturing cells according to an exemplary embodiment.

FIG. 1 is a diagram showing an overview of apparatus for culturing cells 1 according to an exemplary embodiment of the present invention. The apparatus for culturing cells according to the present exemplary embodiment includes at least first holder 3, pump 4, first shifter 5, second holder 11, second shifter 16, and controller 15. First holder 3 is, for example, a pipet holder, and holds pipet 2 (a pipet chip) by a resilient member such as a spring. First shifter 5 including a track 5a and a guide 5b is, for example, a pipet shifter, and shifts pipet 2 held by first holder 3. Second holder 11 is, for example, a culture vessel holder, and holds a plurality of culture vessels 10 by projections 11a. Second shifter 16 is a culture vessel shifter such as a manipulator including arms 16a that wrap around to grip and shift culture vessel 10. Controller 15 controls the operation of the structures in the apparatus. Control by controller 15 is exerted in accordance with a preset condition, or a condition input from operation unit 13 such as a touch panel.

Pipet 2 is connected to pump 4 via first holder 3. Pipet 2 discharges/draws a liquid by being powered by pump 4. First shifter 5 shifts first holder 3 within the apparatus. First storage 6 is, for example, a spare pipet storage, and stores spare pipets 2. Second storage 7 is, for example, a waste pipet storage into which pipet 2 is placed after use to be discarded. Tube holder 9 holds a plurality of tubes 8. Tubes 8 are containers that store various types of liquids. One tube 8 stores a culture medium for replacement, and other tube 8 stores a dissociation solution. Second holder 11 can hold culture vessel 10. Tank 12 is, for example, a waste water tank into which a culture medium is placed after use to be discarded. Second shifter 16 can grip and shift culture vessel 10. Note that, second holder 11 can hold a plurality of culture vessels 10. Further, by allowing second holder 11 to rotate, the positions of a plurality of culture vessels 10 can be changed.

On the vertical upper side of first storage 6, first lid 6a being a lid for spare pipets is provided. On the vertical upper side of tube holder 9, third lid 9a being a lid for the tubes is provided. On the vertical upper side of second storage 7, second lid 7a being a lid for the waste pipets is provided. On the vertical upper side of tank 12, fourth lid 12a being a lid for the tank is provided.

First lid 6a and third lid 9a are provided for preventing entry of surrounding dust or liquids into spare pipets 2 or tubes 8. On the other hand, second lid 7a and fourth lid 12a are provided for preventing liquids in discarded pipets 2 or waste liquids from splattering on surroundings. Culture vessel 10 is provided with lid 10a.

When pipet 2 draws a liquid (such as a culture medium or a dissociation solution) in culture vessel 10 or discharges a liquid (such as a culture medium or a dissociation solution) into culture vessel 10, the lid of culture vessel 10 is opened by being once lifted toward the vertical upper side by second shifter 16, and thereafter translationally shifted in a horizontal direction.

Further, apparatus for culturing cells 1 includes centrifuge 14, heater 17, refrigerator 18, incubator 19, and third storage 20. Centrifuge 14 centrifuges a culture medium containing cells, to separate the culture medium and the cells from each other. Heater 17 heats the culture medium, and refrigerator 18 stores a reagent such as a culture medium in tube 8 or the like under low temperatures. Incubator 19 cultures cells in culture vessel 10 under prescribed conditions. Third storage 20 stores spare culture vessels 10. Third storage 20 is, for example, a culture vessel storage, and stores empty culture vessels 10.

Refrigerator 18, incubator 19 and third storage 20 are arranged at positions not preventing second shifter 16 from shifting culture vessel 10. Further, heater 17 and centrifuge 14 are arranged at positions where pipet 2 held by first holder 3 and the tip of second shifter 16 can shift.

Next, with reference to FIG. 2, a description will be given of the operation of replacing a culture medium by apparatus for culturing cells 1 according to the present exemplary embodiment. Note that, as described above, each operation of apparatus for culturing cells 1 (each step shown in FIG. 2) is controlled by controller 15.

Figure 2:
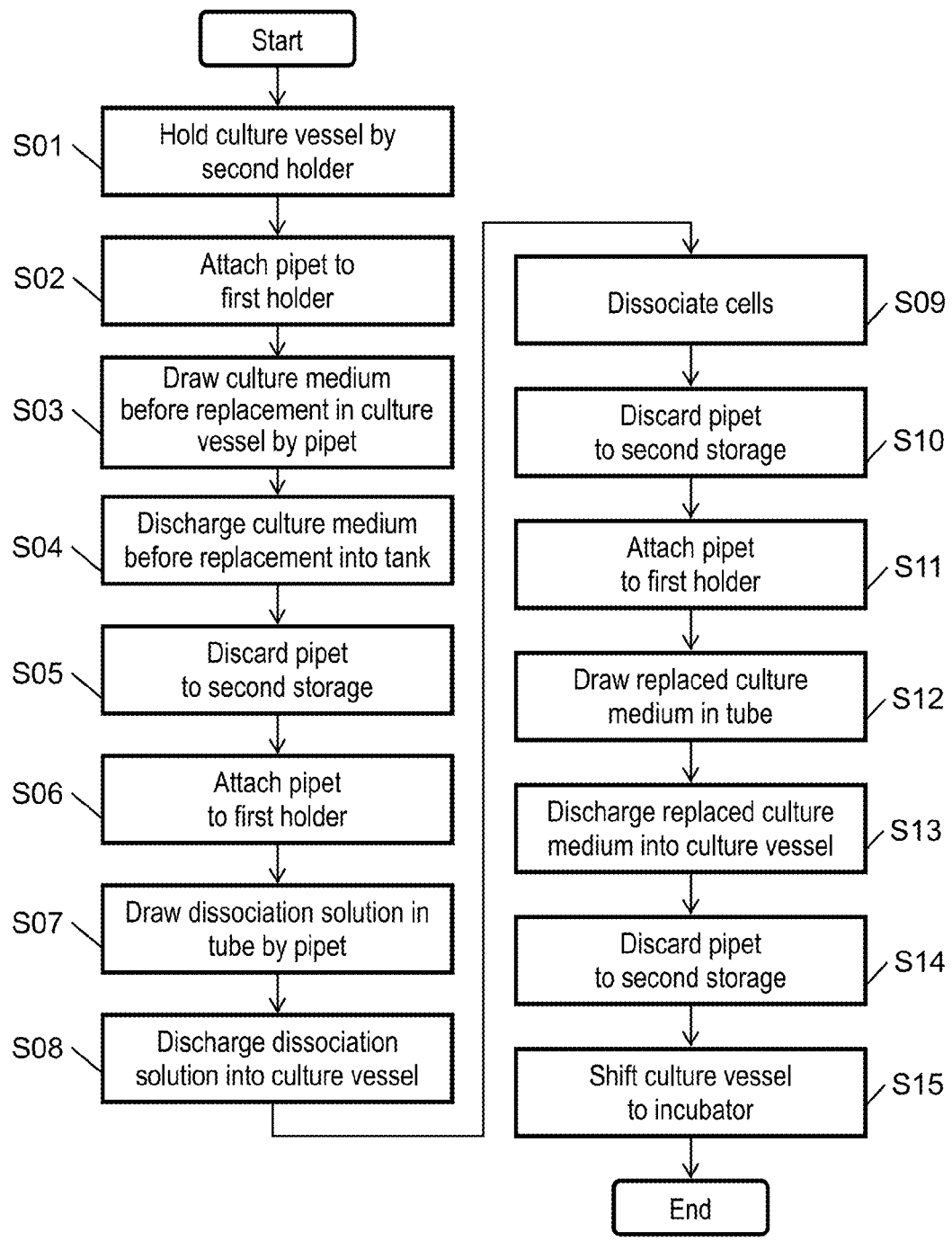
FIG. 2 is a flowchart of culture medium replacement according to the exemplary embodiment.

When an instruction to start replacing a culture medium is issued from controller 15, in Step S01 in FIG. 2, firstly, second shifter 16 opens a door of incubator 19. Next, second shifter 16 takes out targeted culture vessel 10 out of a plurality of culture vessels 10 stored in incubator 19. Then, second shifter 16 shifts targeted culture vessel 10 to above second holder 11, and holds targeted culture vessel 10 by second holder 11. Thereafter, the door of incubator 19 is closed by an open-close mechanism built in incubator 19.

Note that, in the present exemplary embodiment, while the description has been given of the example where culture vessel 10 containing cells being cultured is stored in incubator 19, culture vessel 10 may be taken out from other storage (for example, third storage 20 or the like) as necessary.

Next, in Step S02, first shifter 5 shifts first holder 3 to above first storage 6. Then, first lid 6a is opened, and first holder 3 holds first pipet 2 out of a plurality of pipets 2 stored in first storage 6. Thereafter, by an open-close mechanism built in first storage 6, first lid 6a is closed. Pipet 2 is inserted into first holder 3 and fixed, and thereby first holder 3 holds pipet 2.

Next, in Step S03, first shifter 5 shifts first holder 3 to above second holder 11. Then, second shifter 16 translationally shifts lid 10a of culture vessel 10 in a horizontal direction immediately before draw-in or discharge. Lid 10a translationally shifts in the horizontal direction to be opened. In this state, by a draw-in operation powered by pump 4, first pipet 2 draws a culture medium in culture vessel 10 before replacement. Thereafter, lid 10a of culture vessel 10 is returned to the original position by first shifter 5. In this manner, since a draw-in or discharge operation is performed with lid 10a not fully opened, the possibility of entry of dust or the like into the culture medium in culture vessel 10 can be reduced. In the present exemplary embodiment, since lid 10a is translationally shifted in the horizontal direction, the possibility of entry of dust or the like inner than lid 10a can be reduced.

Next, in Step S04, first shifter 5 shifts first holder 3 to above tank 12. Then, in a state where fourth lid 12a is opened by an open-close mechanism built in tank 12, the culture medium before replacement having been drawn into first pipet 2 is discharged into tank 12 by a discharge operation powered by pump 4 thereby discarded. Thereafter, fourth lid 12a is closed by the open-close mechanism.

Next, in Step S05, first shifter 5 shifts first holder 3 to above second storage 7. Then, second lid 7a is opened by an open-close mechanism built in second storage 7, and used first pipet 2 is put in second storage 7 thereby discarded. Thereafter, second lid 7a is closed by the open-close mechanism. The operation of discarding pipet 2 is as follows. In a state where pipet 2 is gripped by actuator 7b (shown in FIG. 6) of second storage 7, when first holder 3 is shifted right and left, rotation moment is generated at pipet 2. Pipet 2 is removed from first holder 3 using this rotation moment, and put in second storage 7 thereby discarded. Note that, how to remove pipet 2 will be detailed later with reference to FIG. 6.

Next, in Step S06, by the procedure similar to Step S02, second pipet 2 is inserted into first holder 3 and held.

Next, in Step S07, first shifter 5 shifts first holder 3 to above tube holder 9. Then, third lid 9a is opened by an open-close mechanism built in tube holder 9, and by a draw-in operation powered by pump 4, second pipet 2 draws a cell dissociation solution in tube 8. Thereafter, third lid 9a is closed by the open-close mechanism. The cell dissociation solution is a liquid for dissociating cells attached onto culture vessel 10. As the cell dissociation solution, for example trypsin is used.

Next, in Step S08, first shifter 5 shifts first holder 3 to above second holder 11. Then, second shifter 16 translationally shifts lid 10a of culture vessel 10 in the horizontal direction. In a state where lid 10a has translationally shifted, by a discharge operation powered by pump 4, second pipet 2 discharges the dissociation solution into culture vessel 10. Thereafter, lid 10a of culture vessel 10 is returned to the original position.

Next, in Step S09, by a shaking mechanism built in second holder 16, culture vessel 10 is shaken, and cells are dissociated from culture vessel 10.

Next, in Step S10, first shifter 5 shifts first holder 3 to above second storage 7. Then, by the open-close mechanism built in second storage 7, second lid 7a is opened, and used second pipet 2 is put in second storage 7 thereby discarded. Thereafter, second lid 7a is closed by the open-close mechanism.

Next, in Step S11, by the procedure similar to Step S02, first holder 3 holds third pipet 2.

Next, in Step S12, first shifter 5 shifts first holder 3 to above tube holder 9. Then, by the open-close mechanism built in tube holder 9, third lid 9a is opened. Then, by a draw-in operation powered by pump 4, third pipet 2 draws a replaced culture medium (new culture medium) in tube 8. Thereafter, third lid 9a is closed by the open-close mechanism.

Next, in Step S13, first shifter 5 shifts first holder 3 to above second holder 11. Then, second shifter 16 translationally shifts lid 10a of culture vessel 10 in the horizontal direction. In a state where lid 10a has translationally shifted (in a state where lid 10a is opened), by a discharge operation powered by pump 4, pipet 2 discharges the replaced culture medium (new culture medium) into culture vessel 10. Thereafter, lid 10a of culture vessel 10 is returned to the original position by second shifter 16.

Note that, pipet 2 is preferably vibrated during the discharge operation to promote drainage of the culture medium. Thus, formation of a drop is suppressed.

Next, in Step S14, first shifter 5 shifts first holder 3 to above second storage 7. Then, by the open-close mechanism built in second storage 7, second lid 7a is opened, and used third pipet 2 is put in second storage 7 thereby discarded. Thereafter, by the open-close mechanism, the second lid 7a is closed.

Next, in Step S15, after the door of incubator 19 is opened by an open-close mechanism built in incubator 19, second shifter 16 shifts culture vessel 10 into incubator 19, and stores in incubator 19. Thereafter, the door of incubator 19 is closed by the open-close mechanism.

In connection with apparatus for culturing cells 1 according to the present exemplary embodiment, under control of controller 15, the culture medium is replaced through the flow described above with reference to FIG. 2.

Note that, at any one of time points after Step S01, after Step S03, and after Step S13, it is preferable to capture an image inside culture vessel 10 by a camera for observation. When observation is made at such time points, the amount of culture medium before and after replacement, and type and amount of dissociation solution can be adjusted in accordance with the observation result. Hence, the precision of cell culture can be further improved.

Next, a detailed description will be given of part of the structures of apparatus for culturing cells 1 according to the present exemplary embodiment and part of the flow shown in FIG. 2.

Figure 3:
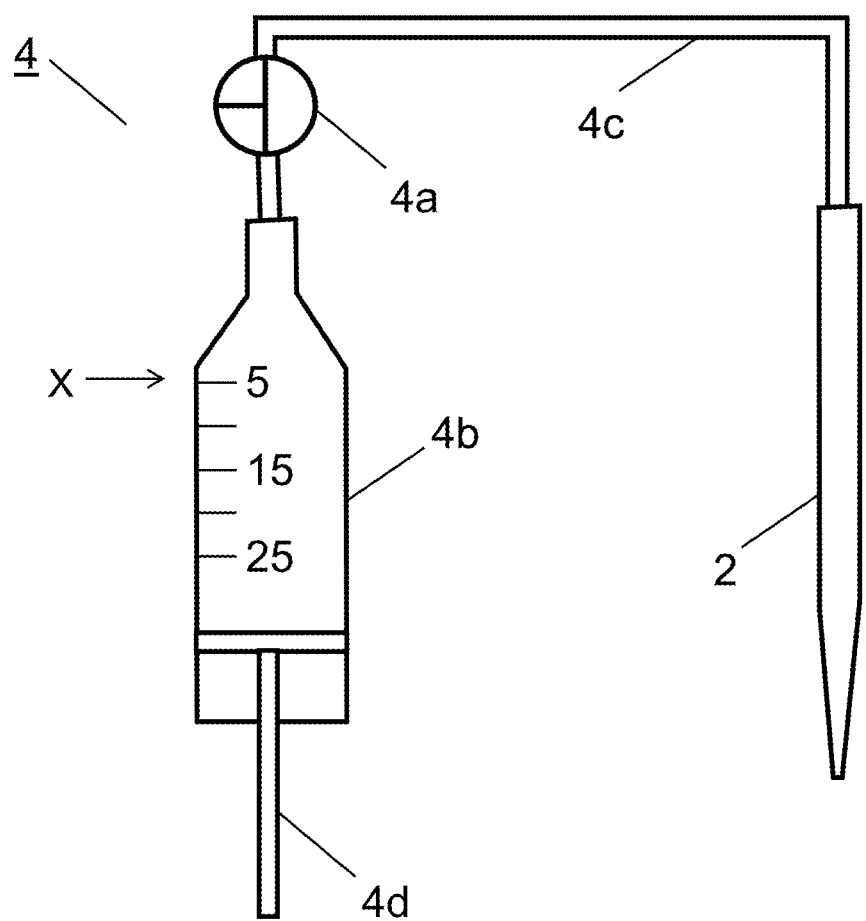
FIG. 3 is a diagram showing an overview of a pump according to the exemplary embodiment.

With reference to FIG. 3, a description will be given of pump 4 of apparatus for culturing cells 1 according to the present exemplary embodiment. As shown in FIG. 3, pump 4 according to present exemplary embodiment is, for example, a syringe pump, and structured by three-way valve 4a, syringe 4b, and channel 4c. For example, the origin position of syringe 4b whose volume is 25 ml is set at the position of 5 ml, instead of 0 ml. The origin position is represented by X in FIG. 3. That is, in the present exemplary embodiment, the origin position of plunger 4d of syringe 4b is set to the position shifted in a draw-in direction by a prescribed amount than the discharge threshold position. This is because plunger 4d is preferably shifted in a discharge direction exceeding the origin position when discharge is performed, for causing pipet 2 to fully discharge the liquid. Controller 15 controls pump 4 to perform the setting of the origin position. That is, controller 15 controls pump 4 such that the origin position of pump 4 is set at the position shifted in the draw-in direction from the discharge threshold position.

Note that, syringe 4b and pipet 2 communicate with each other by channel 4c via three-way valve 4a. When three-way valve 4a is switched to the open side (the pipet 2 side), syringe 4b returns to the origin position. In the present exemplary embodiment, when pipet 2 draws a liquid (a culture medium or a dissociation solution), in a state where pipet 2 is inserted into tube 8, three-way valve 4a is once switched to the open side. Then, pump 4 draws the air. Thereafter, three-way valve 4a is switched to the open side (the pipet 2 side) and plunger 4d is returned to the origin position. Thereafter, a liquid (a culture medium or a dissociation solution) in tube 8 is drawn. When the liquid (the culture medium or the dissociation solution) remains at the tip of pipet 2, a film is formed at the tip of pipet 2. Therefore, the foregoing operation is performed for the purpose of preventing formation of the film.

Figure 4A:
FIG. 4A is a diagram showing a state where liquid discharge has completed in the present exemplary embodiment.
Figure 4B:
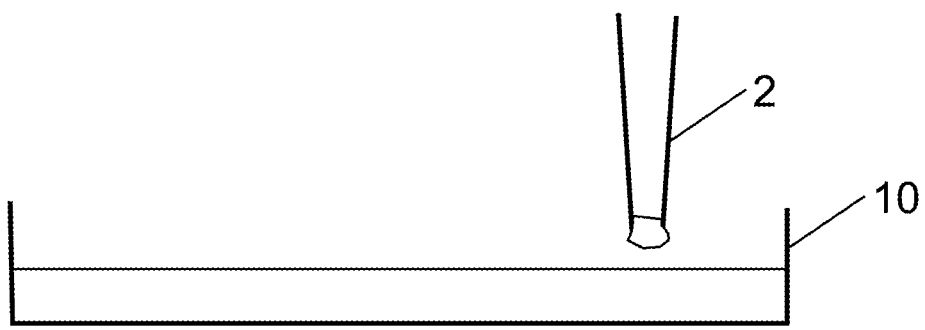
FIG. 4B is a diagram showing a state where liquid discharge has completed in Reference Example.
Figure 5A:
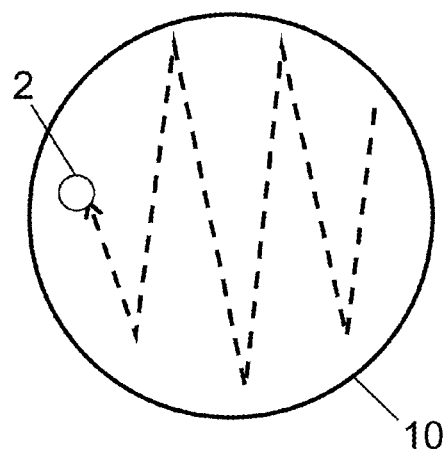
FIG. 5A is a schematic plan view at a first dissociation solution discharge according to the exemplary embodiment.
Figure 5C:
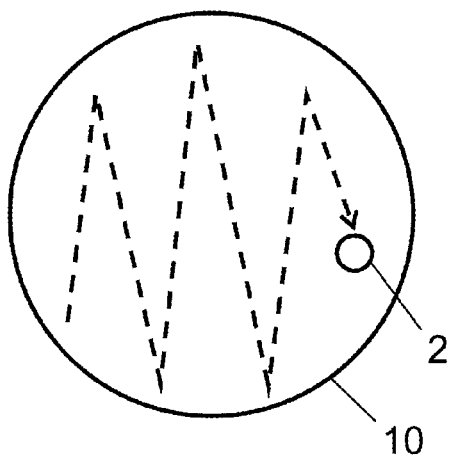
FIG. 5C is a schematic plan view at a second dissociation solution discharge according to the exemplary embodiment.
Figure 5B:
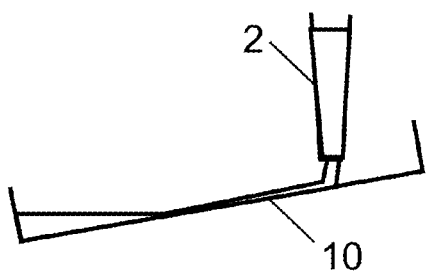
FIG. 5B is a schematic side view at the first dissociation solution discharge according to the exemplary embodiment.
Figure 5D:
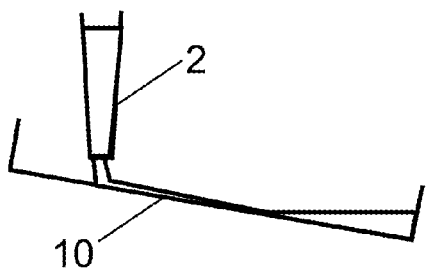
FIG. 5D is a schematic side view at the second dissociation solution discharge according to the exemplary embodiment.

Next, with reference to FIGS. 4A and 4B, a detailed description will be given of the discharge operation in Step S13 in FIG. 2. In the present exemplary embodiment, as shown in FIG. 4A, discharge of a liquid (a culture medium) completes in a state where the tip of pipet 2 is positioned at the surface of the culture medium. That is, when discharge of a liquid has completed, the tip of pipet 2 is positioned at the surface of the liquid (the culture medium). Controller 15 controls first shifter 5 to control the position of the tip of pipet 2. By setting the position of the tip of pipet 2 to the surface of the culture medium, as shown in Reference Example in FIG. 4B, generation of a drop or a bubble in the culture medium can be suppressed.

Next, with reference to FIGS. 5A to 5D, a detailed description will be given of the discharge operation in Step S08 in FIG. 2. In the present exemplary embodiment, discharge of the dissociation solution is performed twice, and culture vessel 10 is tilted in the first direction during the first discharge and in the second direction opposite to the first direction during the second discharge. At the discharge start time point, the dissociation solution is discharged to the inner wall surface of culture vessel 10 on the vertical upper side. In this manner, by setting the inner wall surface on the vertical upper side of the culture vessel to the discharge start position, it becomes less likely that the dissociation solution is directly discharged to cells at the discharge start time. Thus, any possible damage to cells can be reduced.

Further, as described above, as shown in FIGS. 5B and 5D, culture vessel 10 is tilted in the first direction during the first discharge (see FIG. 5B) and in the second direction opposite to the first direction during the second discharge (see FIG. 5D). With culture vessel 10 set in this state, pipet 2 discharges the dissociation solution while moving from the higher position in the tilted plane of culture vessel 10 to the lower position.

By allowing the dissociation solution to flow in culture vessel 10 by such an operation of pipet 2, any possible damage to the cells in culture vessel 10 can be suppressed.

Figure 6:
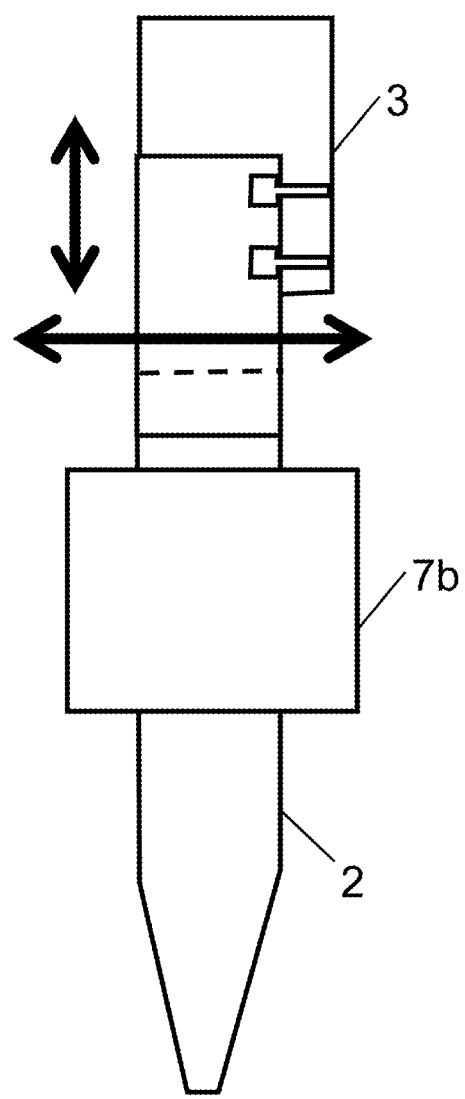
FIG. 6 is a diagram for describing removal of a pipet according to the exemplary embodiment.

Next, with reference to FIG. 6, a detailed description will be given of an operation of removing pipet 2 in Steps S05, S10, and S14 in FIG. 2. When pipet 2 held by first holder 3 is removed, pipet 2 is gripped by doughnut-shaped actuator 7*b* provided at second storage 7. Thereafter, first holder 3 is shaken in a direction perpendicular to the axis of pipet 2 (in the right-left direction) while being pulled upward by a prescribed amount. In this manner, by first holder 3 being moved right and left while being pulled upward, pipet 2 is removed in a manner similarly to the case where a lid of a bottle is removed, for example. In the case where pipet 2 is removed without first holder 3 being moved right and left, the force required for removing pipet 2 becomes greater than the force required to attach pipet 2. Further, in this case, the attached constituents may be displaced by the shock of removal of pipet 2. In contrast, by the above-described method according to the present exemplary embodiment, pipet 2 can be removed smoothly. Controller 15 controls first shifter 5 when pipet 2 is removed from first holder 3, such that first holder 3 moves right and left while shifting upward.

Figure 7:
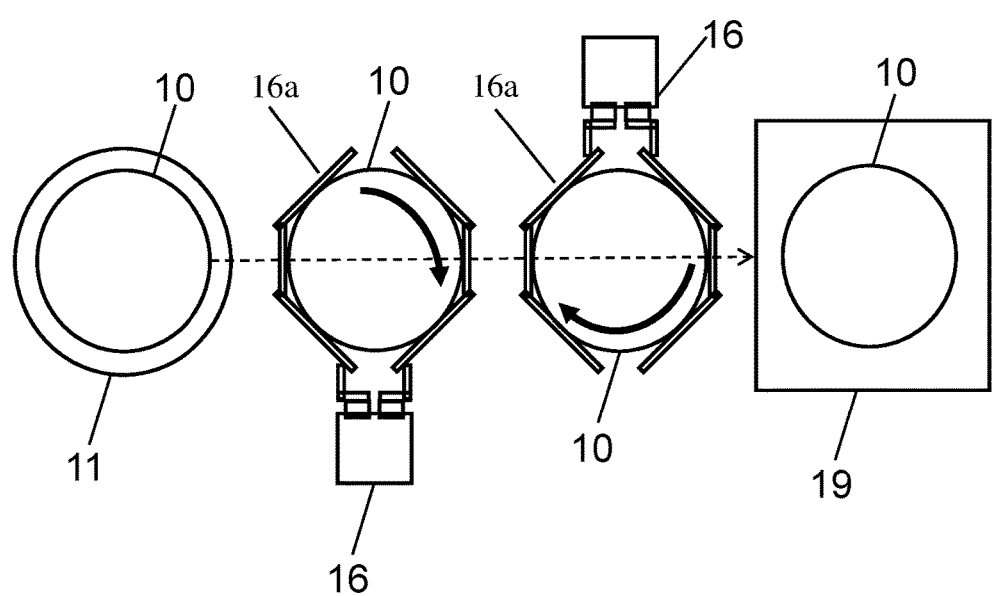
FIG. 7 is a diagram for describing a state where a culture vessel is shifted according to the exemplary embodiment.
Figure 8:
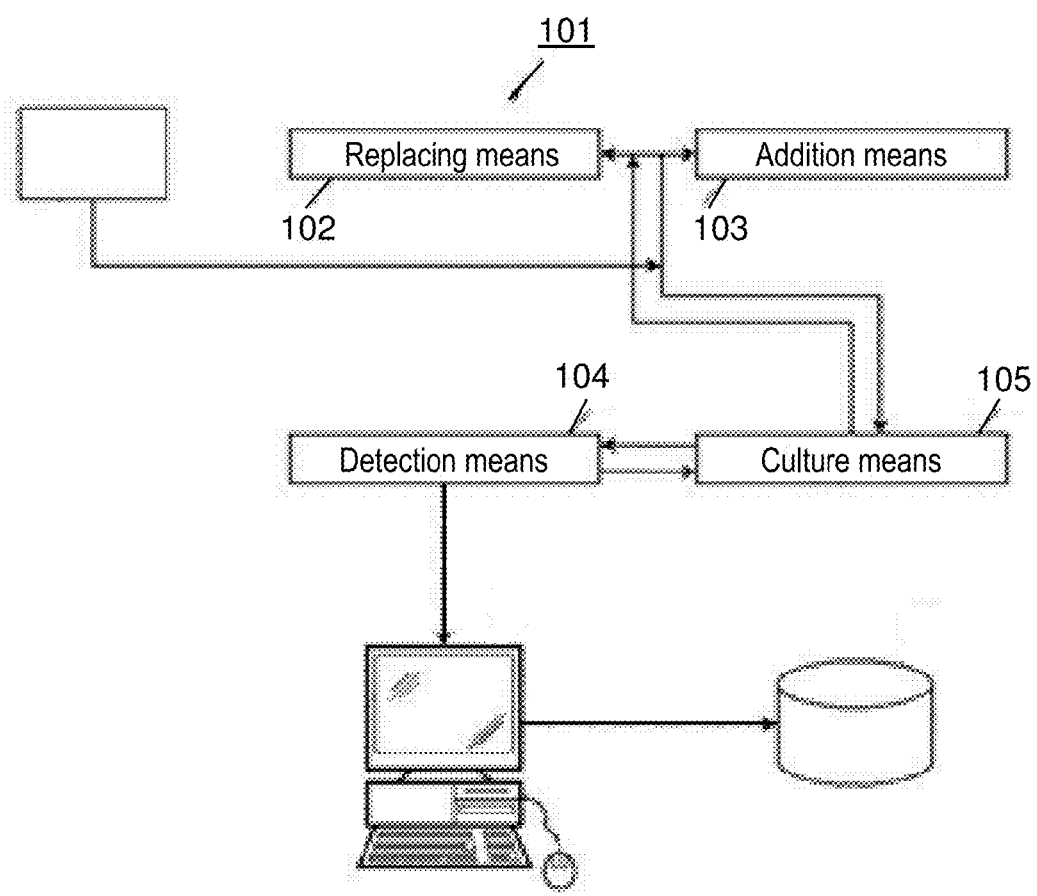
FIG. 8 is a schematic diagram showing a conventional apparatus for culturing cells.

Further, with reference to FIG. 7, a detailed description will be given of an operation of second shifter 16 for shifting culture vessel 10. When culture vessel 10 shifts relative to second holder 11, by reaction or inertia of the shift, a force in a certain direction is applied to a culture medium or cells in culture vessel 10. Hence, in this case, cells in culture vessel 10 may be unevenly located. Accordingly, in the present exemplary embodiment, for the purpose of preventing uneven location of cells, second shifter 16 is shifted while culture vessel 10 is rotated, as shown in FIG. 7. That is, in the present exemplary embodiment, when culture vessel 10 is shifted, the phase orientation of culture vessel 10 is dynamically changed in accordance with the shifting track. Controller 15 controls second shifter 16 such that culture vessel 10 shifts relative to second holder, and that culture vessel 10 shifts while rotating.

Preferably, second shifter 16 not only rotates culture vessel 10, but also shifts culture vessel 10 vertically downward. It is considered that, by allowing culture vessel 10 to shift downward, the possibility of uneven location of cells can further be reduced. Controller 15 controls second shifter 16 such that, when culture vessel 10 shifts relative to second holder 11, culture vessel 10 shifts vertically downward while rotating.

INDUSTRIAL APPLICABILITY

The apparatus for culturing cells of the present invention is useful in cell culture in regenerative medicine and drug discovery fields.

The invention claimed is:

1. An apparatus for culturing cells using a culture medium in a culture vessel, the apparatus comprising:
a pump connected to a pipet held by a first holder;
a first shifter affixed to the first holder, the first shifter including a track and a guide structure configured to shift the first holder in a vertical direction and in a horizontal direction;
a second holder including projections, the second holder configured to hold the culture vessel and tilt the culture vessel;
a second shifter including a manipulating device comprising arms configured to wrap around and grip and shift a lid of the culture vessel in a horizontal direction; and
a controller programmed to control a movement of the first shifter and the second shifter and control an inclination of the second holder,
wherein the controller is programmed to control the pipet to draw a liquid from the culture vessel or to discharge a liquid into the culture vessel and to control the second shifter to translationally shift the lid of the culture vessel in a horizontal direction to open the lid;
the controller is programmed to discharge the dissociation solution into the culture vessel twice and control the second holder to tilt the culture vessel in a first direction during a first discharge and in a second direction opposite to the first direction during a second discharge, and
the controller is programmed to control the first shifter to cause an inner wall surface of the culture vessel on a vertical upper side to become a discharge start position in the first discharge and in the second discharge.

2. The apparatus for culturing cells according to claim 1, wherein a position to which a tip of the pipet faces moves from a higher position in a tilted surface of the culture vessel toward a lower position.

3. The apparatus for culturing cells according to claim 1, wherein the controller is programmed to control the second shifter to shift the culture vessel relative to the second holder, and to shift the culture vessel while rotating.

4. The apparatus for culturing cells according to claim 3, wherein the controller is programmed to control the second shifter to shift the culture vessel vertically downward when the culture vessel shifts relative to the second holder.

5. The apparatus for culturing cells according to claim 1, wherein the controller is programmed to control the first shifter to position the tip of the pipet at a surface of the culture medium in the culture vessel when the discharge of the liquid into the culture vessel completes.

6. The apparatus for culturing cells according to claim 1, wherein the controller is programmed to control the first shifter to move the first holder right and left while shifting upward relative to the pipet when the pipet is removed from the first holder.

7. The apparatus for culturing cells according to claim 1, wherein the controller is programmed to control the pump to set an origin position of the pump to a position shifted in a draw-in direction from a discharge threshold position.

8. The apparatus for culturing cells according to claim 1, further comprising:
a first storage configured to store a spare pipet;
a tube holder configured to hold a tube containing the culture medium;
a tank configured to discard the culture medium; and
a second storage configured to store a waste pipet, wherein
the first storage, the tube holder, the tank, and the second storage are each provided with a lid.

* * * * *